US00RE36348E

United States Patent [19]

Carter et al.

[11] E Patent Number: Re. 36,348

[45] Reissued Date of Patent: Oct. 19, 1999

[54] METHOD AND APPARATUS FOR CHANGING BRAIN WAVE FREQUENCY

[75] Inventors: John Leland Carter, Harris County; Harold Laverne Russell, Galveston County, both of Tex.; Len Ochs, Contra Costa County, Calif.

[73] Assignee: Neurotrain L.C., Galveston, Tex.

[21] Appl. No.: 08/490,116

[22] Filed: Jun. 12, 1995

Related U.S. Patent Documents

Reissue of:

[64] Patent No.: 5,036,858
Issued: Aug. 6, 1991
Appl. No.: 07/497,426
Filed: Mar. 22, 1990

U.S. Applications:

[63] Continuation of application No. 08/102,472, Aug. 5, 1993, abandoned.

[51] Int. Cl.[6] ..... A61B 5/04

[52] U.S. Cl. ..... 600/545; 600/27

[58] Field of Search ..... 128/731, 732; 600/26–28, 545, 544

[56] References Cited

U.S. PATENT DOCUMENTS

| | | | |
|---|---|---|---|
| 3,884,218 | 5/1975 | Monroe | 600/28 |
| 4,191,175 | 3/1980 | Nagle | 600/27 |
| 4,227,516 | 10/1980 | Meland | 600/26 |
| 4,228,807 | 10/1980 | Yagi et al. | 128/732 |
| 4,315,502 | 2/1982 | Gorges | 600/27 |
| 4,334,545 | 6/1982 | Shiga | 128/732 |
| 4,834,701 | 5/1989 | Masaki | 600/28 |
| 4,883,067 | 11/1989 | Knispel et al. | 128/732 |
| 5,241,967 | 9/1993 | Yasushi et al. | 128/732 |

OTHER PUBLICATIONS

*Mind Power: Alpha,* Radio Electronics, vol. 47, No. 7 pp. 36–39, 91 Jul. 1976, Gernsback Publications Inc., NY, NY.

*Feeback Control of Amount and Frequency of Human Alpha Waves,* Kobayashi et al., Jap. J. Medicene, vol. 14 No. 4 Aug. 1976.

*Primary Examiner*—Robert L. Nasser

*Attorney, Agent, or Firm*—W. Thomas Timmons; Timmons & Kelly

[57] ABSTRACT

A method for changing brain wave frequency to a desired frequency determines a current brain wave frequency of a user, generates two frequencies with a frequency difference of a magnitude between that of the current actual brain wave frequency and the desired frequency but always within a predetermined range of the current actual brain wave frequency, and produces an output to the user corresponding to the two frequencies. One apparatus to accomplish the method has a computer processor, a computer memory, EEG electrodes along with an amplifier, a programmable timing generator responsive to the computer processor for generating the two frequencies, audio amplifiers and a beat frequency generator driving a visual frequency amplifier.

18 Claims, 1 Drawing Sheet

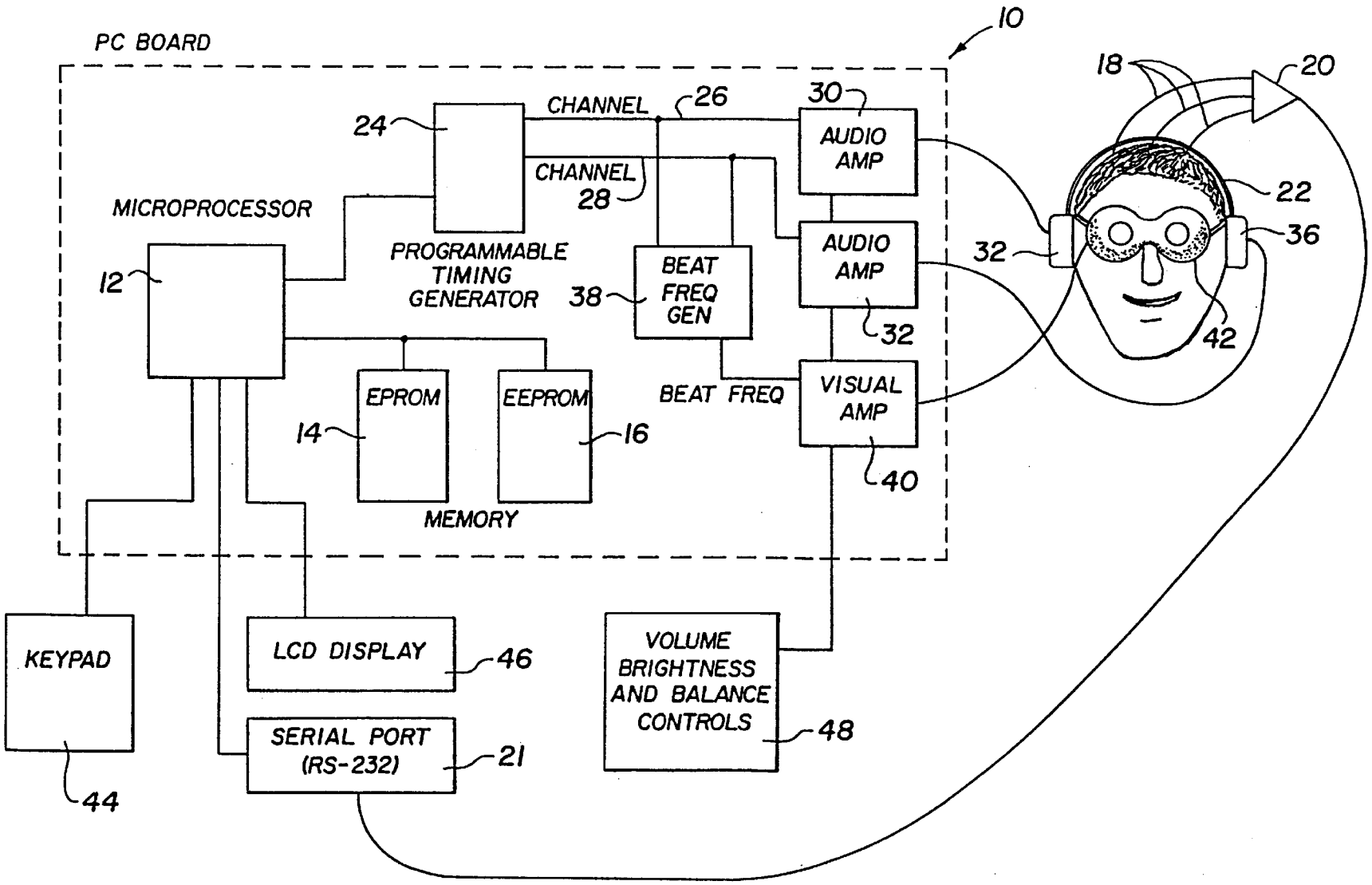
10
PC BOARD
20
22
36
42
18
32
AUDIO AMP
30
AUDIO AMP
32
VISUAL AMP
40
BEAT FREQ GEN
38
BEAT FREQ
CHANNEL
26
CHANNEL
28
PROGRAMMABLE TIMING GENERATOR
24
EEPROM
16
EPROM
14
MEMORY
MICROPROCESSOR
12
VOLUME BRIGHTNESS AND BALANCE CONTROLS
48
LCD DISPLAY
46
SERIAL PORT (RS-232)
21
KEYPAD
44

METHOD AND APPARATUS FOR CHANGING BRAIN WAVE FREQUENCY

Matter enclosed in heavy brackets [ ] appears in the original patent but forms no part of this reissue specification; matter printed in italics indicates the additions made by reissue.

*This application is a continuation of utility application Ser. No. 08/102,472 filed Aug. 5, 1993, abandoned.*

DESCRIPTION

1. Technical Field

The present invention relates generally to methods and apparatus for controlling brain wave frequencies.

The human brain produces detectable signals which vary in strength and frequency over time and from one part of the brain to another at any given time. Different frequencies are associated with different moods and changing abilities. A brain wave frequency of 13 hertz or higher is known as "beta-rhythm" and is normally associated with daily activity when all five sensory organs are functioning. A brain wave frequency of 8 to 13 hertz is known as "alpha-rhythm" and is often associated with a relaxed creative state. Brain wave frequencies of 4 to 8 hertz and 0.5 to 4 hertz are known as "theta-rhythm" and "delta-rhythm" respectively. Theta-rhythm is often found in adolescents with learning disorders, and delta-rhythm is typical of normal sleep. Researchers believe that externally creating brain wave frequencies associated with normal or desired behavior, such as externally creating delta-rhythm in someone who has a problem sleeping or alpha-rhythm in someone who has trouble learning, can help bring about such behavior.

2. Background Art

In the 1960's and early 1970's, Robert Monroe of the Monroe Institute of Applied Sciences explored the effects of sound on the brain and discovered that he could produce a driving or entrainment of brain waves. Dr. Gerald Oster, a biophysicist, also investigating the effects of sound on the brain, discovered that pulsations called binaural beats occurred in the brain when tones of different frequencies were presented separately to each ear. The beat frequency equals the frequency difference between the two tones. Both Monroe and Oster began using electronic oscillators to provide tones with frequency, purity and intensity that can be precisely controlled.

U.S. Pat. No. 3,884,218 to Robert A. Monroe shows a method for inducing sleep by amplitude modulating a pleasing sound with a delta-rhythm signal which is referred to as an "EEG sleep signal."

U.S. Pat. No. 4,191,175 to Nagle shows a method and apparatus for repetitively "producing a noise-like signal for inducing a hypnotic or anesthetic effect . . . " by creating frequency bursts of digital pulses which are then passed through a pink noise filter to get rid of frequencies above a certain cut-off. The resultant signal is then passed through a band pass filter and used to drive an audible signal source.

An apparatus for electrophysiological stimulation is shown in U.S. Pat. No. 4,227,516 to Meland et al. in which a first signal above the delta-beta frequency range is modulated by signal within that range and applied to electrodes on the forehead of a user.

A learning-relaxation device of U.S. Pat. No. 4,315,502 has both lights for pulsing signals and sound means for a pulsing sound signal as well as a control means which can individually vary the light and sound signals.

U.S. Pat. No. 4,834,701 to Masaki shows a device similar to those used by Monroe and Oster with first and second generators with frequencies above 16 hertz and a frequency difference of 4 to 16 hertz sounded to lower the brain wave frequency of a user.

An article entitled "Alpha Brain Waves & Biofeedback Training" in the December 1972 popular Electronics show a system which uses a person's own EEG signal to modulate a tone generator which, in turn, then drives a speaker heard by the same person. The device allowed a person to "hear" his or her own brain signals in an attempt to voluntarily control the frequency. A similar device which allows a person to "see" his or her own brain waves is shown in an article entitled "Mind Power: Alpha" in the July 1976 Radio-Electronics.

DISCLOSURE OF INVENTION

A method for stimulating a user according to the present invention includes first determining a desired brain wave frequency and then determining the actual current brain wave frequency of a user, allowing for the possibility that one user could have more than one brain wave frequency at the same time. First and second signals having first and second frequencies are then generated, the frequency difference being between the current brain wave frequency and the desired brain wave frequency, but also being within a certain range of the current brain wave frequency. An output corresponding to the first and second signals and detectable by the user is then produced. The output can be sound or light or even electrical current. The first and second signals can be combined first before sounding or can be presented separately to, one to each ear, with the resultant binaural beat.

The steps are repeated until the desired brain wave frequency is reached. The procedure then followed depends upon the particular situation. The desired frequency con be maintained for some predetermined period of time, after which a new desired frequency can be determined. One likely replacement for the desired frequency is the original brain wave frequency of the user as it was when the session began. Another possibility would be to take the user to a rest frequency between "work" sessions. Another possibility would be to generate no signal at all for a period of time.

A preferred form of an apparatus according to the present invention for urging the brain wave frequency of a user toward a desired frequency includes a computer processor, a memory which can be written to and read from the computer processor, means such as EEG electrodes attached to the head of the user along with an amplifier for determining a current brain wave frequency of a user, which means communicates with the computer processor, a programmable timing generator responsive to the computer processor, generating at least a first and a second signal, and means detectable by the user for producing an output corresponding to the first and second signals. The frequency difference between the first and second signals is between the current brain wave frequency and the desired brain wave frequency and is within a predetermined range of the current brain wave frequency.

These and other objects, advantages and features of this invention will be apparent from the following description taken with reference to the accompanying drawing, wherein is shown the preferred embodiments of thee invention.

BRIEF DESCRIPTION OF DRAWING

FIG. 1 is a block diagram representation of an apparatus according to the present invention for urging the brain wave frequency of a user toward a desired brain wave frequency.

BEST MODE FOR CARRYING OUT THE INVENTION

Referring now to the drawing, an apparatus according to the present invention is represented generally by reference numeral 10. Apparatus 10 includes a computer processor such as microprocessor 12, memory 14 and 16 which can be written to or read from the microprocessor for storing programs and data, and means such as electrodes 18 and amplifier 20 for determining a current brain wave of a user 22. Electrodes 18 and amplifier 20 communicate with microprocessor 12 by through serial port 21. A programmable timing generator 24 is responsive to microprocessor 12 and generates a first signal at a first frequency on a first channel 26 and a second signal at a second frequency on a second channel 28. The frequency difference between the first and second signals is between the current brain wave frequency and the desired brain wave frequency and is within a predetermined range of the current brain wave frequency. First audio amplifier 30 along with right earphone 32 sounds the first signal to the right ear of the user, and second audio amplifier 34 along with left earphone 36 sounds the second signal to the left ear of the user.

The first and second signals are combined in beat frequency generator 38. The combined signal is then amplified by visual amplifier 40, yielding a beat signal equal to the frequency difference which is used to drive light goggles 42.

Keypad 44 and liquid crystal display 46 are conventional input and output devices, which together with Microprocessor 12 and memory 14 and 16 could form part of a personal or even a lap-top computer. Volume, brightness and balance controls 48 are used to adjust to the individual user and the purpose of the use.

It is now easy to see that a method according to the present invention for stimulating a user includes determining a desired brain wave frequency, then determining a current brain wave frequency of the user, then generating a first signal at a first frequency and a second signal at a second frequency, and then producing an output detectable by the user corresponding to the first and second signals to generate a beat signal equal to the frequency difference. The beat signal can be a binaural beat signal in the head of the user or an electronic beat signal. The steps are repeated until the desired frequency is reached or substantially reached.

One example for use of the present invention for a child experiencing problems in school which are not emotional would be:

original current brain wave frequency=10 Hz
gradually reduce to 5 Hz over 2 to 3 minutes
stay at 5 Hz for 10 to 15 minutes
back to 10 Hz for 2 to 3 minutes
1 minute with no signal
2 minutes at 18 Hz
1 minute with no signal
2 minutes at 10 Hz.

In one sense, such a use could be considered the mental equivalent of a programmable treadmill. Throughout the program illustrated, the signal caused from the frequency difference would be within 10 or 15 percent of the current actual.

From the foregoing it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawing is to be interpreted as illustrative and not in a limiting sense.

We claim:

1. A method for stimulating a user, comprising in combination the steps of:

determining a desired brain wave frequency;

determining a current brain wave frequency of the user;

generating a first signal at a first frequency;

generating a second signal at a second frequency *creating a frequency difference between the first frequency and the second frequency* wherein the frequency difference [between the first and second signals] is between the current brain wave frequency and the desired brain wave frequency and is within a predetermined range of the current brain wave frequency; and producing an output detectable by the user corresponding to the first and second signals to generate a beat signal equal to the frequency difference.

2. A method according to claim 1 further comprising:

repeating the steps of determining a current brain wave frequency, generating a first signal, generating a second signal, and producing an output detectable by the user corresponding to the first and second signals to generate a beat signal equal to the frequency difference until the current brain wave frequency is within a predetermined range of the desired brain wave frequency, further comprising:

maintaining the difference between the first and second frequencies substantially equal to the desired brain wave frequency for a predetermined amount of time; and changing the desired brain wave frequency to a second desired brain wave frequency and repeating the steps of determining a current brain wave frequency, generating a first signal, generating a second signal, and producing an output detectable by the user corresponding to the first and second signals to generate a beat signal equal to the frequency difference until the current brain wave frequency is within a predetermined range of the desired brain wave frequency.

3. A method according to claim 2 wherein the step of producing an output detectable by the user corresponding to the first and second signals to generate a beat signal equal to the frequency difference comprises sounding the first and second signals.

4. A method according to claim 2 wherein the second desired brain wave frequency substantially equals the original current brain wave frequency.

5. A method according to claim 1 further comprising:

repeating the steps of determining a current brain wave frequency, generating a first signal, generating a second signal, and producing an output detectable by the user corresponding to the first and second signals to generate a beat signal [equal to] *at* the frequency difference until the current brain wave frequency is within a predetermined range of the desired brain wave frequency, further comprising:

maintaining the difference between the first and second frequencies substantially equal to the desired brain wave frequency for a predetermined amount of time; and producing no output detectable by the user for a second predetermined amount of time.

6. An apparatus for urging the brain wave frequency of a user toward a desired brain wave frequency, the apparatus comprising in combination:

means for determining a current brain wave frequency of the user;

means for generating a first signal at a first frequency;

means for generating a second signal at a second frequency wherein [the] *there is a* frequency difference between the first *frequency* and *the* second [signals] *frequency and the frequency difference* is between the current brain wave frequency and the desired brain wave frequency and is within a predetermined range of the current brain wave frequency; and means for producing an output detectable by the user corresponding to the first and second signals to generate a beat signal [equal to] *at* the frequency difference.

7. An apparatus according to claim 6 wherein the means for producing an output detectable by the user corresponding to the first and second signals to generate a beat signal [equal to] *at* the frequency difference comprises means for sounding the first and second signals.

8. An apparatus for urging the brain wave frequency of a user toward a desired brain wave frequency, the apparatus comprising in combination:

a computer processor;

[a memory which can be written to and read from the computer processor;]

means *in communication with the computer processor* for determining a current brain wave frequency of the user[, which communicates with the computer processor];

a programmable timing generator *operatively connected to and* responsive to the computer processor [and] *for* generating a first signal at a first frequency and a second signal at a second frequency wherein [the] *there is a* frequency difference between the first *frequency* and *the* second [signals] *frequency and the frequency difference* is between the current brain wave frequency and the desired brain wave frequency and is within a predetermined range of the current brain wave frequency; *and* means *responsive to the programmable timing generator and* detectable by the user for producing an output corresponding to the first and second signals.

9. An apparatus according to claim 8 wherein the means detectable by the user is a means for sounding the first and second signals.

10. An apparatus according to claim 8 wherein the means detectable by the user comprises a means for generating a beat signal [equal to] *at* the frequency difference [of the first and second signals].

11. An apparatus according to claim 10 wherein the means detectable by the user further comprises light means *for visual detection by the user,* responsive to the means for generating a beat frequency.

*12. A method for stimulating a user, comprising in combination the steps of:*

*determining a desired brain wave frequency;*

*determining a current brain wave frequency of the user;*

*generating a signal at a frequency between the current brain wave frequency and the desired brain wave frequency which is within a predetermined range of the current brain wave frequency; and*

*producing an output detectable by the user at the signal frequency.*

*13. A method according to claim 12 further comprising:*

*repeating the steps of determining a current brain wave frequency, generating a signal at a frequency between the current brain wave frequency and the desired brain wave frequency which is within a predetermined range of the current brain wave frequency, and producing an output detectable by the user at the signal frequency until the current brain wave frequency is within a predetermined range of the desired brain wave frequency, further comprising:*

*maintaining the signal frequency substantially equal to the desired brain wave frequency for a predetermined amount of time; and*

*changing the desired brain wave frequency to a second desired brain wave frequency and repeating the steps of determining a current brain wave frequency, generating a signal at a frequency between the current brain wave frequency and the second desired brain wave frequency which is within a predetermined range of the current brain wave frequency, and producing an output detectable by the user at the signal frequency equal until the current brain wave frequency is within a predetermined range of the second desired brain wave frequency.*

*14. A method according to claim 13 wherein the second desired brain wave frequency substantially equals the original current brain wave frequency.*

*15. A method according to claim 12 further comprising:*

*repeating the steps of determining a current brain wave frequency, generating a signal at a frequency between the current brain wave frequency and the desired brain wave frequency which is within a predetermined range of the current brain wave frequency, and producing an output detectable by the user at the signal frequency until the current brain wave frequency is within a predetermined range of the desired brain wave frequency, further comprising:*

*maintaining the signal frequency substantially equal to the desired brain wave frequency for a predetermined amount of time; and*

*producing no output detectable by the user for a second predetermined amount of time.*

*16. An apparatus for urging the brain wave frequency of a user toward a desired brain wave frequency, the apparatus comprising in combination:*

*means for determining a current brain wave frequency of the user;*

*means for generating a signal at a frequency between the current brain wave frequency and the desired brain wave frequency which is within a predetermined range of the current brain wave frequency; and*

*means for producing an output detectable by the user at the signal frequency.*

*17. An apparatus for urging the brain wave frequency of a user toward a desired brain wave frequency, the apparatus comprising in combination:*

*a computer processor;*

*means in communication with the computer processor for determining a current brain wave frequency of the user;*

*a programmable timing generator operatively connected to and responsive to the computer processor for generating a signal at a frequency which is between the*

*current brain wave frequency and the desired brain wave frequency and is within a predetermined range of the current brain wave frequency;*

*means responsive to the programmable timing generator and detectable by the user for producing an output at the signal frequency.*

*18. An apparatus according to claim 17 wherein the means detectable by the user comprises light means for visual detection by the user, responsive to the signal frequency.*

* * * * *